US010473637B2

(12) United States Patent
Schoenbach et al.

(10) Patent No.: US 10,473,637 B2
(45) Date of Patent: Nov. 12, 2019

(54) DEVICE AND METHOD FOR DETERMINING THE TEMPERATURE OF A ROAD BUILDING MATERIAL APPLIED BY A CONSTRUCTION MACHINE, AND CONSTRUCTION MACHINE COMPRISING SUCH A DEVICE

(71) Applicant: MOBA Mobile Automation AG, Limburg (DE)

(72) Inventors: Torsten Schoenbach, Limburg (DE); Dominik Becher, Limburg (DE); Marcus Watermann, Limburg (DE); Christian Grasso, Limburg (DE)

(73) Assignee: MOBA-MOBILE AUTOMATION AG, Limburg (DE)

( * ) Notice: Subject to any disclaimer, the term of this patent is extended or adjusted under 35 U.S.C. 154(b) by 711 days.

(21) Appl. No.: 14/924,852

(22) Filed: Oct. 28, 2015

(65) Prior Publication Data
US 2016/0131633 A1 May 12, 2016

(30) Foreign Application Priority Data

Nov. 6, 2014 (DE) .................... 10 2014 222 693

(51) Int. Cl.
*G01J 5/00* (2006.01)
*G01N 33/42* (2006.01)
(Continued)

(52) U.S. Cl.
CPC ............ *G01N 33/42* (2013.01); *E01C 19/48* (2013.01); *G01J 5/0022* (2013.01); *G01J 5/02* (2013.01);
(Continued)

(58) Field of Classification Search
CPC .. G01J 5/00; H04N 5/2621; G01N 2021/1793
(Continued)

(56) References Cited

U.S. PATENT DOCUMENTS 4,646,353 A * 2/1987 Tenge ................ G06K 7/10871
235/437
4,899,296 A * 2/1990 Khattak ................. G01B 11/16
348/148
(Continued)

FOREIGN PATENT DOCUMENTS

CN 202870982 U * 4/2013
DE 10 2008 058 481 A1 7/2009
(Continued)

OTHER PUBLICATIONS

English language abstract of DE 20 2009 016 129 U1.
(Continued)

*Primary Examiner* — Gail Kaplan Verbitsky
(74) *Attorney, Agent, or Firm* — Keating & Bennett, LLP

(57) ABSTRACT

A device for determining the temperature of a road building material applied by a construction machine in a mounting width is arranged at the construction machine in a range within the mounting width and has an infrared temperature measuring head, a motor and a controller, the infrared temperature measuring head being arranged to be twistable by the motor transverse to the direction of travel of the construction machine and being effective to record temperature measuring values of the surface of road building material during a rotational movement at at least two measuring points spaced apart from one another. The controller is effective to control the motor based on the fitting position of the device at the construction machine such that the distance between the measuring points on the surface to be measured remains equal.

11 Claims, 8 Drawing Sheets

(51) Int. Cl.
*G01J 5/04* (2006.01)
*E01C 19/48* (2006.01)
*G01J 5/08* (2006.01)
*G01J 5/02* (2006.01)
*G01N 21/17* (2006.01)
*H04N 5/262* (2006.01)

(52) U.S. Cl.
CPC .............. *G01J 5/047* (2013.01); *G01J 5/089* (2013.01); *G01N 2021/1793* (2013.01); *H04N 5/2621* (2013.01)

(58) Field of Classification Search
USPC .................................... 374/120, 121, 141, 6
See application file for complete search history.

(56) References Cited

U.S. PATENT DOCUMENTS

| | | | |
|---|---|---|---|
| 4,904,996 A * | 2/1990 | Fernandes | G01R 15/142 340/601 |
| 6,271,878 B1 * | 8/2001 | Sera | G01N 25/72 348/164 |
| 6,749,364 B1 | 6/2004 | Baker et al. | |
| 6,923,080 B1 * | 8/2005 | Dobler | B60R 1/00 348/E7.086 |
| 7,602,947 B1 * | 10/2009 | Lemelson | B60Q 1/0023 340/426.1 |
| 7,828,478 B2 * | 11/2010 | Rege | G01J 5/0022 250/338.1 |
| 8,110,803 B2 * | 2/2012 | Hollander | G01J 5/02 250/338.1 |
| 8,576,286 B1 * | 11/2013 | Childs | G01C 21/00 348/113 |
| 9,950,677 B2 * | 4/2018 | Poliquin | H04N 5/2252 |
| 2004/0207515 A1 * | 10/2004 | Chung | B60Q 9/008 340/435 |
| 2008/0212414 A1 * | 9/2008 | Mardirossian | G07F 17/246 368/90 |
| 2008/0259730 A1 * | 10/2008 | Di Federico | E01C 19/006 367/118 |
| 2009/0066791 A1 * | 3/2009 | Ono | H04N 5/23238 348/143 |
| 2009/0142133 A1 | 6/2009 | Glee et al. | |
| 2009/0147072 A1 * | 6/2009 | Brotherton-Ratcliffe | G03H 1/268 348/40 |
| 2010/0189498 A1 * | 7/2010 | Doherty | G08G 1/096811 404/72 |
| 2012/0218411 A1 * | 8/2012 | Wu | G01N 25/72 348/148 |
| 2012/0261850 A1 * | 10/2012 | Simon | B29C 49/4823 264/40.6 |
| 2013/0322702 A1 * | 12/2013 | Piemonte | G06T 15/005 382/113 |
| 2014/0055602 A1 * | 2/2014 | Childs | G01C 21/00 348/118 |
| 2014/0277939 A1 * | 9/2014 | Ren | G01C 21/3638 701/36 |
| 2014/0308073 A1 | 10/2014 | Delius | |
| 2014/0308074 A1 | 10/2014 | Rutz et al. | |
| 2014/0328371 A1 * | 11/2014 | Buisson | G01K 13/00 374/141 |
| 2014/0341250 A1 * | 11/2014 | Lynam | B60H 1/00785 374/28 |
| 2015/0345907 A1 * | 12/2015 | Varga | F41G 3/147 89/41.05 |
| 2016/0042235 A1 * | 2/2016 | Buschmann | G06T 7/0004 348/148 |
| 2016/0061755 A1 * | 3/2016 | Delius | E01C 19/48 374/43 |
| 2016/0281304 A1 | 9/2016 | Rutz et al. | |
| 2017/0218574 A1 * | 8/2017 | Coe | C08K 5/42 |
| 2017/0322088 A1 * | 11/2017 | Becher | G01J 5/089 |
| 2017/0370775 A1 * | 12/2017 | Kusukame | G01J 5/28 |

FOREIGN PATENT DOCUMENTS

| | | | | |
|---|---|---|---|---|
| DE | 20 2009 016 129 U1 | | 3/2010 | |
| DE | 20 2013 001 597 U1 | | 6/2013 | |
| DE | 102016207584 B3 * | | 6/2017 | ............. E01C 19/48 |
| EP | 2 982 951 A1 | | 2/2016 | |
| EP | 2 990 531 A1 | | 3/2016 | |
| JP | 61135842 A * | | 6/1986 | |
| JP | 03-199502 A | | 8/1991 | |
| JP | 07-003441 A | | 1/1995 | |
| JP | 07-034411 A | | 2/1995 | |
| JP | 2005-097958 A | | 4/2005 | |
| JP | 2007233948 A * | | 9/2007 | |
| JP | 2007-256099 A | | 10/2007 | |
| JP | 2014-206043 A | | 10/2014 | |
| JP | 2014-206044 A | | 10/2014 | |
| KR | 2011129999 A * | | 12/2011 | |
| KR | 101241865 B1 * | | 3/2013 | |
| WO | WO 9500820 A1 * | | 1/1995 | ............. G01C 11/025 |
| WO | 00/70150 A1 | | 11/2000 | |

OTHER PUBLICATIONS

Official Communication issued in Chinese Patent Application No. 201510753512.X, dated Apr. 28, 2017.
Official Communication issued in corresponding Japanese Patent Application No. 2015-211663, dated Dec. 2016.

* cited by examiner

DEVICE AND METHOD FOR DETERMINING THE TEMPERATURE OF A ROAD BUILDING MATERIAL APPLIED BY A CONSTRUCTION MACHINE, AND CONSTRUCTION MACHINE COMPRISING SUCH A DEVICE

CROSS-REFERENCE TO RELATED APPLICATION

This application claims priority from German Patent Application No. 102014222693.7, filed Nov. 6, 2014, which is incorporated herein by reference in its entirety.

BACKGROUND OF THE INVENTION

The present invention relates to the field of construction machines, in particular to a device for determining the temperature of a road building material, such as asphalt, bitumen, asphalt blend material or the like, newly applied by a construction machine, in particular a road finishing machine, in a mounting width, the device being arranged at the construction machine in a region within the mounting width and the device comprising an infrared temperature measuring head, a motor and a controller, the infrared temperature measuring head being arranged to be twistable by the motor transverse to the direction of travel of the construction machine and being effective to record temperature measuring values of the surface of the road building material during a rotational movement at at least two measuring points spaced apart from one another.

Furthermore, the present invention relates to a construction machine comprising such a device.

With road building projects, such as building a new road or renewing damaged road surfaces, the quality of the newly applied road building material is to be documented by the executing companies using check tests. Measuring the temperature of the asphalt layer directly after being mounted by the road finishing machine is among these tests. The temperature of the newly applied road building material is measured over the entire mounting width directly behind the asphalt plank of the road finishing machine.

A lane temperature monitoring system comprising a temperature sensor is known from WO 2000/70150 A1. The temperature sensor here may either by a thermal-imaging camera, a thermal scanner or a thermal-imaging camera operating in a "line scan" mode. The temperature sensor is arranged at the back end of a road finishing machine such that the entire width of the newly applied asphalt layer is scanned. The recorded temperature values may be displayed graphically on a display device.

Disadvantages with such a temperature sensor is the fact that a thermal-imaging camera or thermal scanner is usually very expensive to buy. In particular, for smaller building companies such an investment usually cannot be realized due to the high costs. Furthermore, it is disadvantageous that the detection or opening angles of a thermal-imaging camera or a thermal scanner are highly limited such that, with mounting or installation widths in a range of 8 to 12 meters, for example, a correspondingly adapted objective lens has to be applied at the thermal-imaging camera in order to be able to detect the entire mounting width of the newly applied road building material. This, in turn, increases the cost of such a temperature sensor further. Alternatively, both the thermal-imaging camera and the thermal scanner would have to be applied in a correspondingly elevated position at the road finishing machine, i.e. a lot more than four meters above the surface of the newly applied road building material, in order to be able to detect the entire mounting width of the newly applied road building material. However, this is of particular disadvantage when passing below bridges.

However, when mounting the thermal-imaging camera or thermal scanner at the road finishing machine in an advantageous region of 3 to 4 meters above the surface of the newly applied road construction material, due to the limited detection or opening angle, a correspondingly flat fitting angle relative to the surface of the newly applied road building material is necessitated (cf. FIG. 2, large fitting angle $\gamma_F$) in order for the entire mounting width of the newly applied road building material to be detected. However, the temperature of the newly applied road building material over the entire mounting width is not measured directly behind the asphalt plank of the road finishing machine but in a correspondingly large distance to the back edge of the asphalt plank. Consequently, the temperature values measured no longer correspond to the actual values in the region directly behind the asphalt plank.

A device, as described above, for measuring the temperature of the surface of hot asphalt, including an infrared temperature measuring head moving transverse to the direction of travel, a motor for moving this sensor and a controller, is known already from DE 20 2009 016 129 U1.

Based on this device, calculating the mounting width of the newly applied asphalt layer is known from DE 20 2013 001 597 U1. Same is calculated using the height of the measuring head above the asphalt layer, which is determined using a distance sensor, and the angle values where the measuring head changes its direction of movement.

When recording the temperature measuring values by means of the known device, however, the result is not a steady measuring point pattern. When the fitting position and/or the fitting angles of the device change, so does the distance between the measuring points on the surface of the newly applied road building material. In addition, the distance between the measuring points in the direction of travel of the construction machine changes with a changing speed of travel of the construction machine. If same moves faster, the distance between the measuring points in the direction of travel will become larger.

Consequently, an object of the invention is to provide a simple and cheap device allowing temperature measuring values of newly applied road building material to be recorded over a large mounting width in a region directly behind a construction machine, in particular behind an asphalt plank of a road finishing machine, in a steady measuring point pattern.

SUMMARY

According to an embodiments, a device for determining the temperature of a road building material, such as asphalt, bitumen, asphalt blend material or the like, applied by a construction machine, in particular a road finishing machine, in a mounting width, the device being arranged at the construction machine in a region within the mounting width, may have: an infrared temperature measuring head, a motor and a controller, the infrared temperature measuring head being arranged to be twistable by the motor in a direction transverse to the direction of travel of the construction machine and being effective to record temperature measuring values of the surface of the road building material during a rotational movement at at least two measuring points spaced apart from one another, characterized in that the controller is effective to control, when fitting the device at the construction machine in the region within the mounting width, the motor based on the fitting position of the device at the construction machine such that the distance between the measuring points on the surface to be measured remains steady.

Another embodiment may have a construction machine, in particular a road finishing machine, having at least one device as mentioned before, wherein the device is arranged in the back region and/or in the front region of the construction machine.

In accordance with embodiments, the controller is effective to control the motor additionally based on the fitting angles of the device at the construction machine.

Thus, a predetermined or preset distance of 25 cm, for example, between two measuring points transverse to the direction of travel of the construction machine is maintained on the surface of the newly applied road building material over the entire mounting width, irrespective of the fitting position and the fitting angles of the device. When the fitting position and/or fitting angles of the device are changed, exemplarily when rebuilding a tool at the machine, i.e. the device is shifted in height and/or transverse to the direction of travel of the construction machine and/or the fitting angles of the device are changed, the preset distance of 25 cm, for example, between two measuring points transverse to the direction of travel of the construction machine will be maintained over the mounting width even after changing the fitting position and/or the fitting angles.

In accordance with embodiments, this is achieved by the fact that, with a changing fitting position and/or changing fitting angles of the device, the motor controller is adapted correspondingly and, thus, the predetermined or set distance between two measuring points transverse to the direction of travel of the construction machine is restored and advantageously kept nearly equal.

Advantageously, the infrared temperature measuring head may be tilted by a very large angle, exemplarily in a range of about 120° to 130°. Thus, it is possible, using the inventive device, to detect temperature measuring values in a large region of a mounting width of up to 14 meters directly behind the asphalt plank of a road finishing machine, with an advantageous fitting height of the device in the region of 3 to 4 meters above the surface of the newly applied road building material. The inventive device thus is not limited only to the field of large mounting widths, but, due to the variable twisting angle of the infrared temperature measuring head, may be used instead for all the mounting widths of a road surface in the region mentioned before. Compared to thermal-imaging cameras or thermal scanners, this is advantageous since these usually comprise a fixed detection or opening angle. In addition, the road finishing machine here may pass below bridges, or the like, without any problem.

Of further advantage are the simple fitting of the device at the construction machine and the moderate costs of the individual components of the device and, correspondingly, the entire device. In particular, an infrared temperature measuring head is many times cheaper compared to a thermal-imaging camera or a thermal scanner. This means that purchasing the inventive device is also affordable for smaller building companies.

Thus, it is possible using the inventive device for a steady number of measuring points to be present for determining the temperature of the newly applied road building material with a steady mounting width of the newly applied road building material.

The requirement of having a steady number of measuring points or a steady distance between two measuring points will surely be a topic in biddings for road building projects, exemplarily for building a new road or renewing damaged road surfaces, in order to achieve steady and, thus, comparable quality measurements of the newly applied road building material.

In accordance with embodiments, the speed of movement of the infrared temperature measuring head changes as a function of the speed of travel of the construction machine. This means that an equal distance between the measuring points in the direction of travel of the construction machine, i.e. an equal distance between the series of measurements, is achieved on the surface of the newly applied road building material, irrespective of the speed of travel of the construction machine. When, for example, the distance between the series of measurements, i.e. the measuring points in the direction of travel of the construction machine, is 25 cm, when increasing the speed of travel of the construction machine, the speed of movement of the infrared temperature measuring head has to be increased as well and vice versa.

In order to achieve an approximately steady distance between the series of measurements, the controller for the motor or an evaluating unit arranged at the device or at the construction machine is advantageously connected electrically to the construction machine control computer or a displacement measuring means arranged at the construction machine, such as, for example, a travel wheel which is usually employed in road finishing machines. The speed value achieved in this way may then be used for calculating the speed of movement of the infrared temperature measuring head. Calculating the speed of movement of the infrared temperature measuring head may take place either in the controller for the motor or in the evaluating unit arranged at the device or at the construction machine.

The advantage of adapting the speed of movement of the infrared temperature measuring head to the speed of travel of the construction machine is such that a homogeneous network of measuring points results in connection with an equal measuring point distance transverse to the direction of travel of the construction machine, i.e. in the direction of movement of the infrared temperature measuring head. Only as many measuring points are recorded by the infrared temperature measuring head as are necessitated for illustrating and taking down the measured temperature measuring value, exemplarily on a control computer and/or a display and operating unit connected thereto. Post-processing the recorded temperature measuring value, exemplarily by the control computer, such as discarding or cancelling measuring values or series of measurements no longer required or an interpolation of measuring values or series of measurements, may be omitted. A quantity of data to be transmitted, limited to a minimum, is also of advantage for transmitting the data to different construction machines, such as, for example, a roller, in order to illustrate the data for the roller controller on a display unit in a compressed and easy manner.

Compared to a thermal-imaging camera or a thermal scanner, this is advantageous since these usually exhibit a very high resolution. Usually, many more measuring points are recorded than are necessitated for illustrating and taking down the measured temperature measuring values, exemplarily on a control computer and/or a display and operation unit connected thereto. The result here may be a high quantity of data which has to be processed by the control computer.

In accordance with embodiments, the direction of movement of the infrared temperature measuring head changes as soon as the measured temperature falls below a predetermined minimum value, exemplarily 80° C., at at least one measuring point. The infrared temperature measuring head which is moved by the motor transverse to the direction of travel of the construction machine continually measures the surface temperature of the newly applied road building material. The temperature values are usually in a range of 120 to 170° C. At positions where temperature values in the range of 80 to 120° C. are measured, the road building material mounted has been too cold—a so-called "cold spot" forms in the newly applied road layer, which decreases the temperature of the road surface. However, if the infrared temperature measuring head measures a temperature of less than 80° C., for example, it can be assumed that one of the two outer edges, i.e. the lateral end of the newly applied road layer, has been reached.

It is also possible for a so-called "cold spot" to be in a range below the predetermined minimum value of 80° C., for example. In order to avoid a premature and, possible, erroneous change in the direction of movement of the infrared temperature measuring head in this case, the infrared temperature measuring head is at first moved until the outer edge determined previously has been reached and the recorded temperature measuring values of the presently performed series of measurements are compared to the values of at least one of the series of measurements recorded before.

When at least a temperature value which is above the predetermined minimum value, i.e. above 80° C., for example, is determined at the measuring points in the edge region of the road surface, i.e. in the region of the outer edges, it can be assumed that the present mounting width has not decreased and that a so-called "cold spot" is present in the newly applied road layer. In this case, the infrared temperature measuring head is advantageously moved to the outer edge determined before, or beyond, until a temperature of less than 80° C., for example, is measured at at least one measuring point. In this case, it can be assumed that one of the two outer edges, i.e. the lateral end of the newly applied road layer, has been reached.

When only temperature values below the predetermined minimum value, i.e. below 80° C., for example, are determined at the measuring points in the region of the outer edges, it can be assumed that either the present mounting width has decreased or that there is a so-called "cold spot" in the edge region of the road surface, i.e. in the region of the outer edges. The infrared temperature measuring head will advantageously decrease the measuring range in the subsequent series of measurements and thus approximate a changed mounting width or outer edge. The infrared temperature measuring head is only twisted until a temperature of less than 80° C., for example, is measured at at least one measuring point. The infrared temperature measuring head then assumes that one of the two outer edges has been reached, i.e. the lateral end of the newly applied road layer.

When decreasing the mounting width, the number of measuring points where the infrared temperature measuring head records measuring values, also decreases due to the equal distance between measuring points. In the opposite case, i.e. when widening the mounting width, the number of measuring points will increase correspondingly.

In accordance with embodiments, the position where the infrared temperature measuring head changes its direction of movement is stored in the controller or an evaluating unit arranged at the device or at the construction machine for calculating the mounting width of the newly applied road building material. The mounting width of the newly applied road building material is than calculated from the stored angular positions of the infrared temperature measuring head and the height and the fitting angles of the device or the infrared temperature measuring head relative to the surface of the newly applied road building material.

In accordance with embodiments, the distance between the measuring points and/or the duration of the temperature measurement at a measuring point may be set. Thus, the distance between two measuring points is set both transverse to the direction of travel of the construction machine and in the direction of travel of the construction machine, advantageously by programming the controller, exemplarily using a control computer or a display and operating unit connected thereto. The time constant of the infrared temperature measuring head, i.e. the duration of the temperature measurement at a measuring point, may also be set, advantageously by programming, exemplarily using a control computer or a display and operating unit connected thereto. It is advantageously possible here to adjust the device to, for example, country-specific requirements. Since, in the US, a new road layer is mounted at a higher speed of travel of the road finishing machine, the duration of the temperature measurement at a measuring point has to be shortened here. Additionally, in the US, the distance between two measuring points is usually about 30 cm, whereas in Germany a measuring point distance of about 25 cm is being forced at present.

In accordance with embodiments, a contactless distance measurer, such as a laser distance measurer, is arranged in the region of the device, by means of which the distance of the infrared temperature measuring head to a measuring point where the infrared temperature measuring head is arranged, in the direction of travel of the construction machine, essentially perpendicularly to the surface of the road building material is measured. Compared to a height measurement by one of the machine operators, exemplarily using a measuring tape, such a distance or range measurement is of advantage since the measured value may be read out on the display and operating unit before beginning the construction works and subsequently be programmed into the controller of the device. Laser sensors operating according to the light run time measurement principle may be used for measuring distances, however, ultrasonic sensors or different sensor technologies may also be used.

In accordance with embodiments, the contactless distance measurer is part of the inventive device. Alternatively, the contactless distance measurer may be an external sensor which is, for example, arranged at a suitable position at the device or at the construction machine and connected to the device.

In accordance with embodiments, the contactless distance measurer is electrically connected to the controller of the device. Compared to manually programming the height value into the controller, exemplarily using a control computer or a display and operating unit connected thereto, it is advantageous for the measured value to be transferred directly from the distance measurer to the controller. Thus, erroneous inputs by one of the machine operators, for example, are avoided.

In accordance with embodiments, the controller is electrically connected to a weather station arranged at the construction machine which exemplarily determines the wind speed, ambient temperature, air humidity, rainfall and/or other ambient parameters in the region of the construction machine. Thus, the weather station transmits the determined measuring values to the controller which, in turn, uses or stores same for further calculations, exemplarily calculating the core temperature of the newly applied road building material.

In accordance with embodiments, the motor is a stepper motor, a servomotor, a direct-current motor or a direct-current motor including a gear unit.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
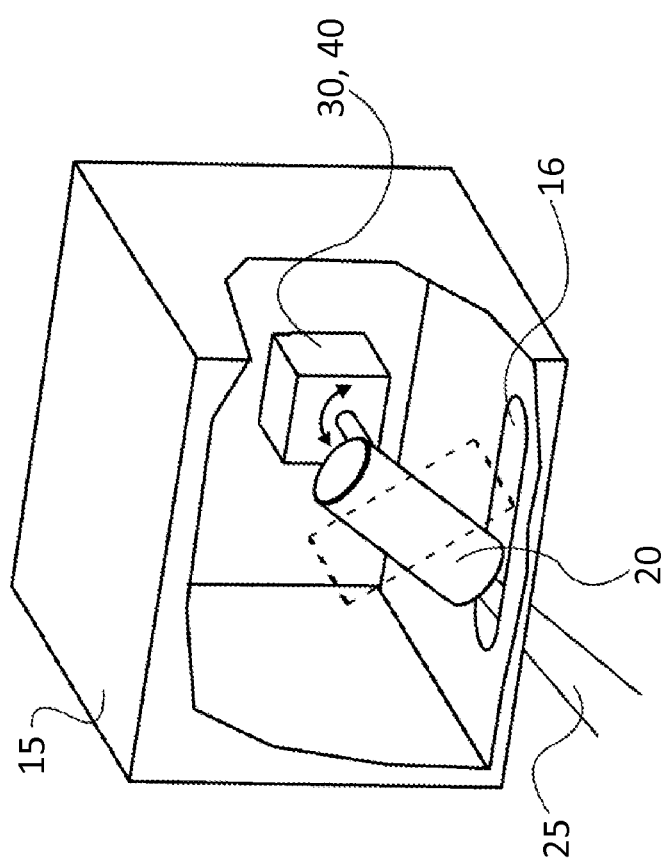
FIG. 1 shows a schematic setup of the inventive device.

In the subsequent description of embodiments, same elements or elements of equal effect will be provided with same reference numerals in the appended drawings.

FIG. 1 schematically illustrates an inventive device which basically consists of a motor 30, an infrared temperature measuring head 20 arranged at the motor 30 or the motor axis, and a controller 40 arranged in the region of the motor 30. All the components mentioned are arranged so as to be protected in a casing 15, the casing 15 comprising an essentially longitudinal opening 16 in its lower region, i.e. in the direction towards the surface 110 of a newly applied road surface (not illustrated here). The fact that the infrared temperature measuring head 20 is arranged at the motor 30 or the motor axis causes the infrared temperature measuring head 20 to be twisted also with a twisting movement of the motor axis. This is indicated schematically in the figure by a broken-line position of the infrared temperature measuring head 20. Advantageously, the infrared temperature measuring head 20 may be twisted in an angular region of about 120° to 130°. During a rotational movement, the infrared temperature measuring head 20 records temperature measuring values through the opening 16 at at least two measuring points 100 to 103 spaced apart from one another on the surface 110 of the newly applied road surface 20 (see, for example, FIG. 3) by means of the infrared radiation 25 emitted from the surface 110.

Figure 2:
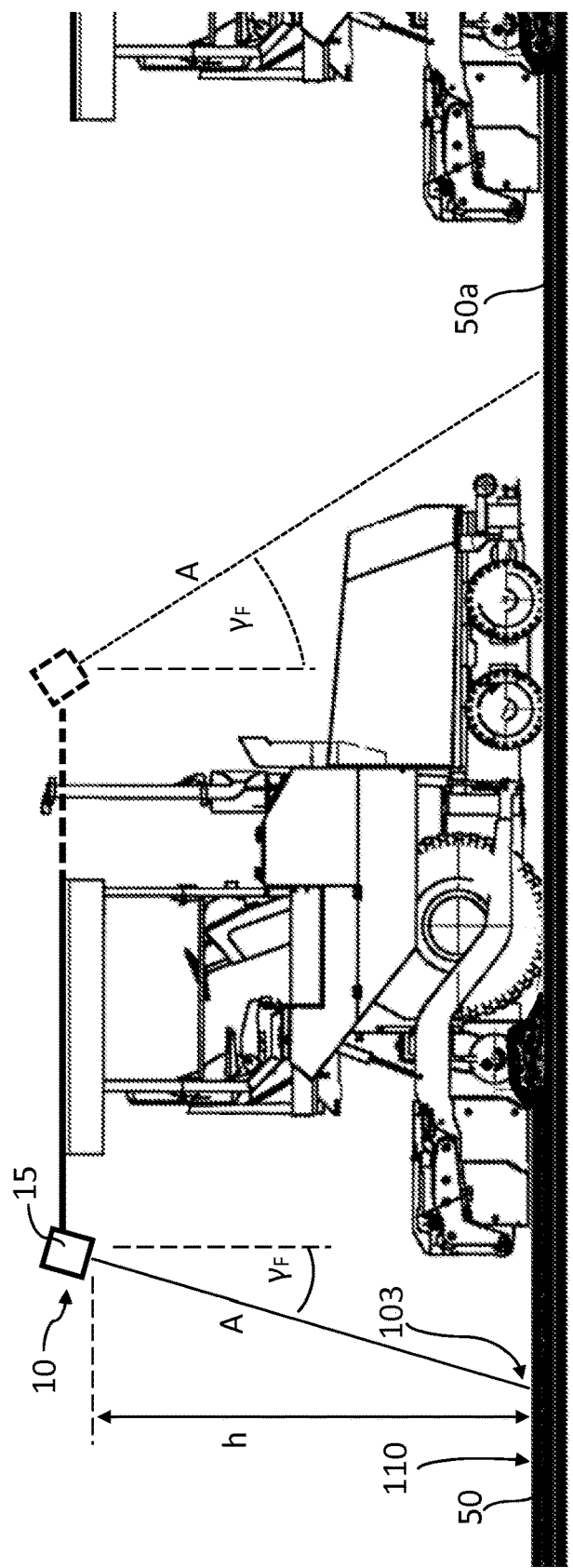
FIG. 2 shows a schematic illustration of a road finishing machine comprising an inventive device each in the front and back regions.

FIG. 2 shows the inventive device which is arranged at a position 10 in the height h to the surface 110 of the newly applied road surface 50 in the back region of a road finishing machine illustrated in side view and also in the front region thereof (illustrated in the figure in broken lines). Usually, the device is fitted only in the back region of the road finishing machine and records temperature measuring values of the newly applied road surface 50. However, it is also feasible for the device to be mounted only in the front region of the road finishing machine which exemplarily mounts an asphalt cover layer, or in addition in the back region. When fitting the device in the front region of the road finishing machine, temperature measuring values of the ground 50a to be asphalted are recorded, irrespective of whether or not a road surface has been mounted before by a different road finishing machine such as, for example, an asphalt binding layer.

As is illustrated in FIG. 2, irrespective of whether it is fitted in the front and/or back region of the road finishing machine, as seen transverse to the direction of travel of the road finishing machine, the device is not arranged at the road finishing machine to be perpendicular to the surface 110, but in a fitting angle $\gamma_F$ in a range of 15° to 30°, for example, relative to a perpendicular line at the road finishing machine. The result is that the distance A schematically illustrated in FIGS. 2 to 6 does not necessarily equal the fitting height h of the device(s) above the surface 110 but that the distance A will be the distance between the device and the measuring point 103 where the infrared temperature measuring head 20 is arranged, in the direction of travel of the construction machine, essentially perpendicularly to the surface 110 of the road building material 50. In order to ensure a measuring precision of +/−3° C., it is advantageous for the infrared temperature measuring head 20 not to be fitted at the road finishing machine beyond a maximum fitting angle $\gamma_F$ of about 45° relative to a perpendicular line.

Figure 3:
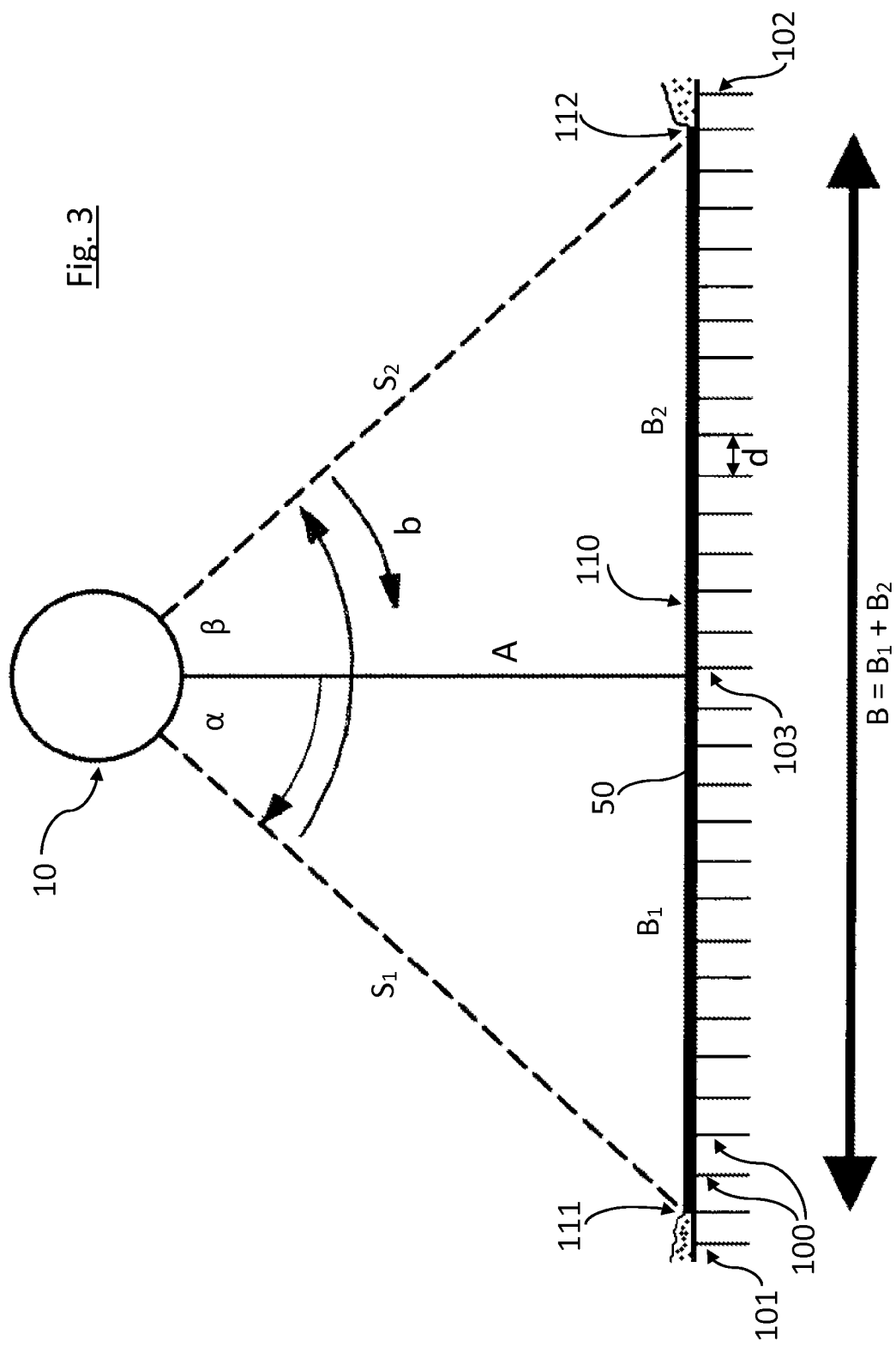
FIG. 3 shows a schematic illustration for illustrating the mode of functioning of the inventive device.

The infrared temperature measuring head 20 illustrated in FIG. 3 moves in the directions of movement indicated by the reference numeral b and records, while moving, temperature measuring values at the measuring points 100 to 103 illustrated in a distance d on the surface 110 of the newly applied road surface 50. The direction of movement of the infrared temperature measuring head 20 changes as soon as the measured temperature falls below a minimum value of 80° C., for example, at one of the measuring points 101 and 102. Thus, the recorded temperature measuring values of the series of measurements performed at present are compared to the values of at least one of the series of measurements recorded before in order to avoid a premature and, possibly, erroneous change in the direction of movement of the infrared temperature measuring head 20. The measuring points 101 and 102 are outside the region where the road building material 50 is applied by the road finishing machine. This region is indicated in FIGS. 3 to 8 by the two outer edges 111 and 112.

In FIGS. 3 to 6, all the measuring points 100 to 103 are schematically indicated to be short, perpendicular lines arranged to one another in a distance d below the newly applied road surface 50. The measuring point 103 is the measuring point where the infrared temperature measuring head 20, in the direction of travel of the construction machine, is arranged essentially perpendicularly to the surface 110 of the road building material 50. In addition, in FIGS. 3 to 6, the region which the infrared temperature measuring 20 moves through is indicated by the outer infrared radiation lines $S_1$ and $S_2$. The two angles $\alpha$ and $\beta$, which each reach from the infrared radiation line $S_1$, $S_2$ to the distance line A, are also defined by this. The controller 40 which controls the motor 30 for twisting the infrared temperature measuring head 20 or an evaluating or calculating unit (not illustrated here) arranged outside the device may calculate the two subsections $B_1=\tan \alpha \times A$ and $B_2=\tan \beta \times A$ from the two angular values $\alpha$ and $\beta$ and from the known distance A of the device or infrared temperature measuring head 20 to the surface 110 of the newly applied road surface 50. The overall mounting width B will subsequently result from adding the two subsections $B_1$ and $B_2$.

Figure 4:
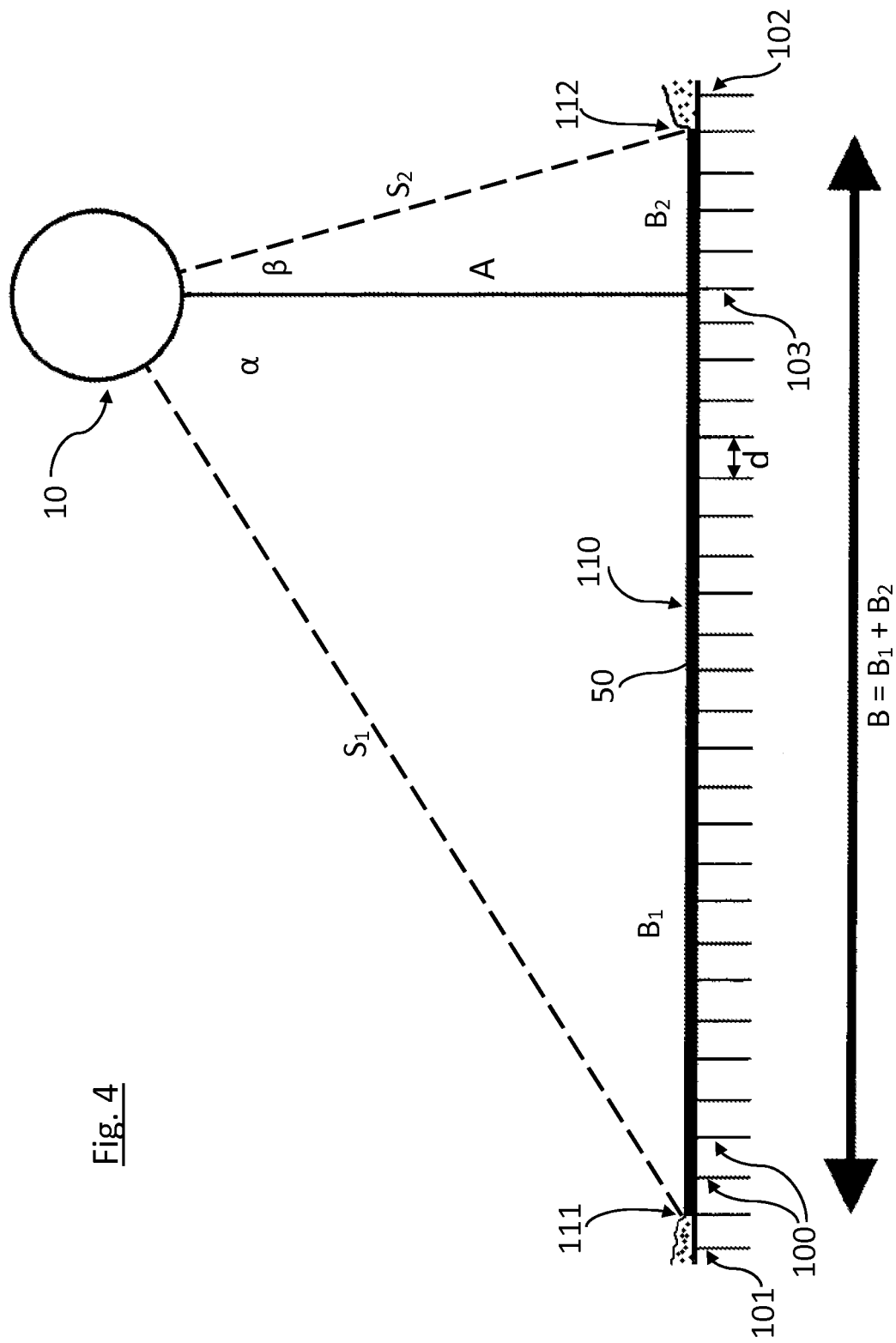
FIG. 4 shows a schematic illustration of the mode of functioning illustrated in FIG. 3, however, with a device arranged to be offset to the right relative to the direction of travel of the construction machine.
Figure 5:
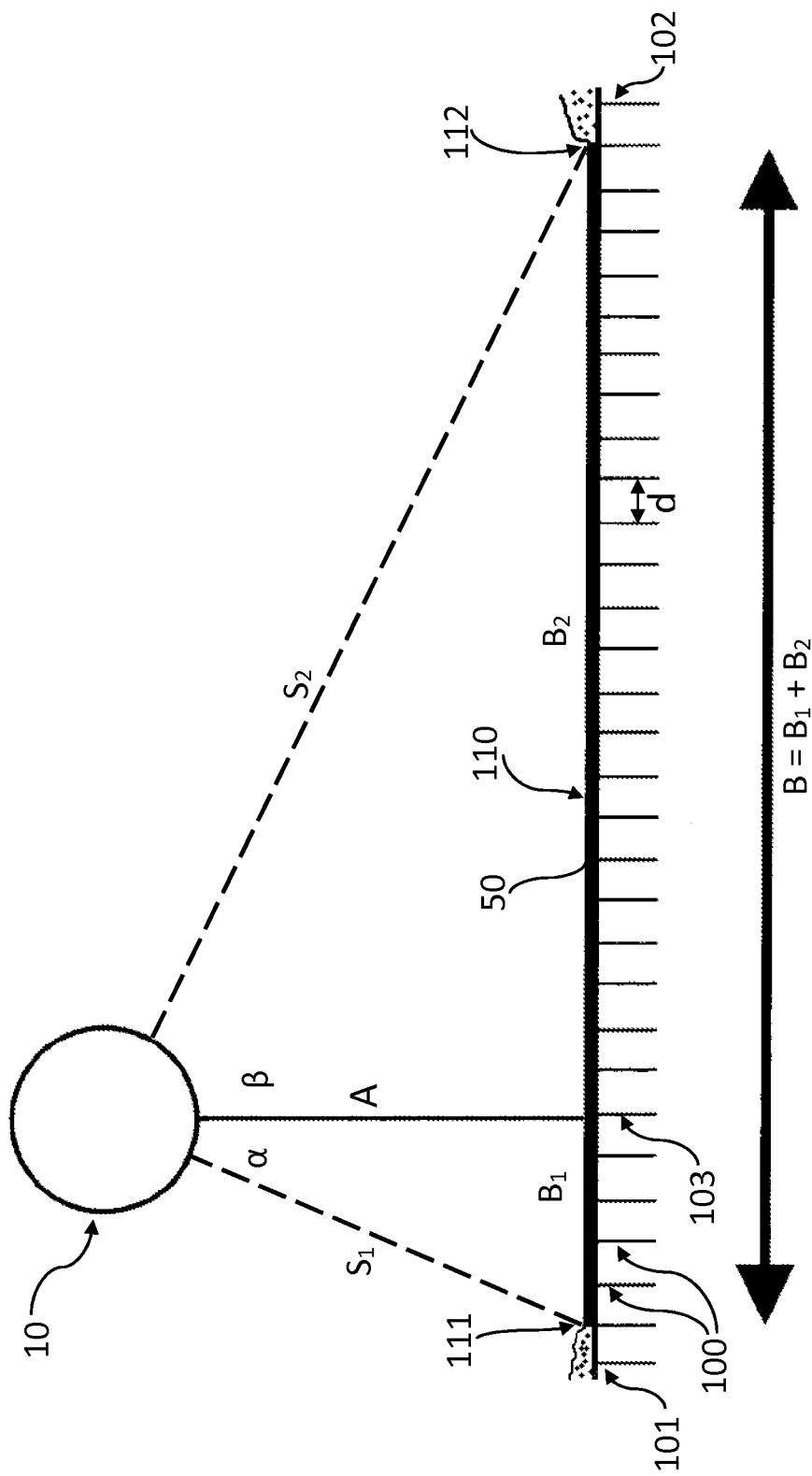
FIG. 5 shows a schematic illustration of the mode of functioning illustrated in FIG. 3, however, with a device arranged to be offset to the left relative to the direction of travel of the construction machine.
Figure 6:
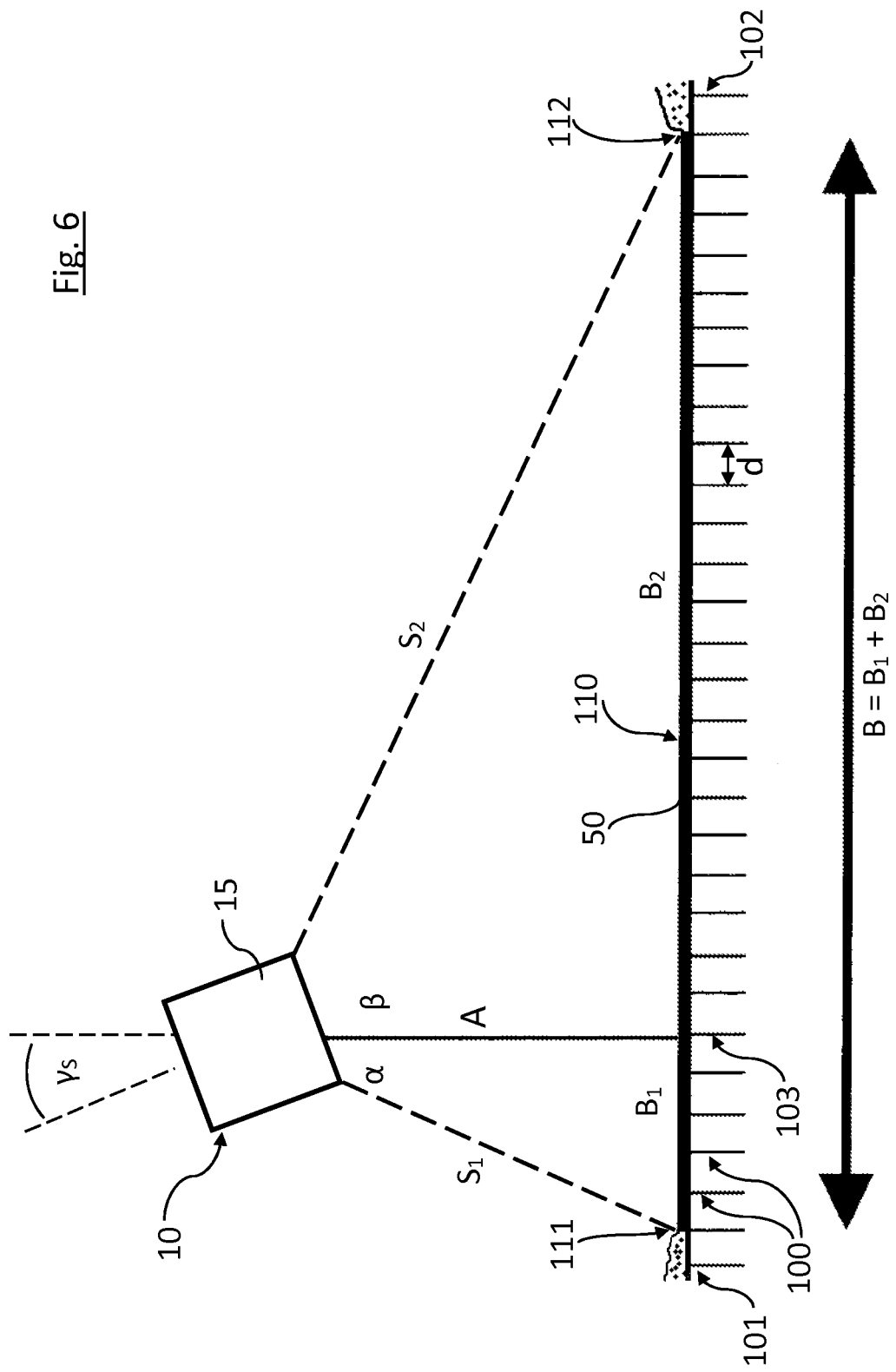
FIG. 6 shows a schematic illustration in accordance with FIG. 5, wherein the device is arranged so as to be twisted by a fitting angle along the scan direction of the infrared temperature measuring head.

Starting from FIG. 3 where the device is arranged to be basically centered transverse to the direction of travel of the construction machine (not shown here), the position 10 of the device at the road finishing machine (not illustrated here) has changed in FIGS. 4, 5 and 6. This means that, in FIG. 4, the device is arranged to be offset to the right relative to the direction of travel of the road finishing machine, whereas, in FIGS. 5 and 6 the device is arranged to the left relative to the direction of travel of the road finishing machine and, additionally, is in a smaller distance A relative to the surface 110 of the newly applied road surface 50. For reasons of simplicity, a steady fitting angle $\gamma_F$ (cf. FIG. 2) of 15°, for example, and a fitting angle $\gamma_S$ of 0° relative to a perpendicular line are assumed in the examples of FIGS. 3 to 6. Thus, the distance A is calculated from $A=(h/\cos 15)$.

In the example in accordance with FIG. 3, an overall width of $(\tan \alpha_{Max} \times (h/\cos 15))+(\tan \beta_{Max} \times (h/\cos 15))=(\tan 60 \times (4/\cos 15))+(\tan 60 \times (4/\cos 15))\approx 14.3$ is detected by the infrared temperature measuring head 20 at a maximum overall twisting angle $\alpha_{Max}+\beta_{Max}$ of, for example, about 120° and a fitting height h of the device or the infrared temperature measuring head 20. With a target detection of a newly applied road surface 50 in a mounting width B of at least 8 meters, it is thus possible to shift the device at the road finishing machine transverse to its direction of travel by more than 3 meters each, starting from the center of the road finishing machine in the direction of the outer edges 111 and 112 such that the mounted road surface 50 is still detected over its entire width B.

In all the embodiments illustrated in accordance with FIGS. 3 to 6, the surface 110 of the newly applied road surface 50 will be detected by the infrared temperature measuring head 20 over the entire mounting width B, even when the overall detection region, due to the large twisting angle of the infrared temperature measuring head 20, is considerably larger than the mounting width B and the device, when seen transverse to the direction of travel of the construction machine, is not arranged in the center as is the case in the embodiments in accordance with FIGS. 4 to 6.

In addition, in all the embodiments illustrated in accordance with FIGS. 3 to 6, the controller 40 of the device is effective to control the motor 30 based on the fitting position 10 and the fitting angles $\gamma_F$ and $\gamma_S$ of the device at the construction machine such that the distance d of the measuring points 100 on the surface 110 to be measured remains equal. This is achieved by the fact that the controller 40 or an evaluating unit (not illustrated here) arranged at the device or at the construction machine calculates the angle $\alpha$ and $\beta$ to be set for the infrared temperature measuring head 20 relative to a perpendicular line, i.e. to a measuring point 103, where the infrared temperature measuring head 20 is arranged, in the direction of travel of the construction machine, essentially perpendicularly to the surface 110 of the road building material 50.

In the example of the embodiment in accordance with FIG. 3, the angles $\alpha$ and $\beta$ are equal and each are about 45°, for example. In addition, a fitting height h of the device or the infrared temperature measuring head 20 to the surface 110 of the newly applied road surface 50 of 4 meters, a measuring point distance d to be set of 25 cm and a starting position of the infrared temperature measuring head 20 in the direction of the outer edge 110 are assumed. Thus, the distances $B_1$ and $B_2$ each are $B_1=B_2=(\tan \alpha \times A)=\tan \alpha \times (h/\cos \gamma_F)=\tan 45 \times (4/\cos 15)\mp 3.86$ meters to the outer edges 111 and 112.

The first measuring point 100 to be recorded in the region of the outer edge 111 is done in a distance of 3.75 meters, starting from a measuring point 103 which represents a so-called zero position for the infrared temperature measuring head 20. Consequently, a first twisting angle $\alpha=\arctan (3.75/(h/\cos \gamma_F))=\arctan (3.75/(4/\cos 15))\approx \arctan 0.91\approx 42.16°$ is set for the infrared temperature measuring head 20. For the following measuring point 100 in a distance $d=0.25$ meters in the direction of the right outer edge 112, a twisting angle of $\alpha=\arctan ((3.75-d)/(h/\cos \gamma_F))=\arctan ((3.75-0.25)/(4/\cos 15))\approx \arctan 0.85\approx 40.20°$ is to be set. The subsequent twisting angle $\alpha$ is $\arctan ((3.75-2d)/(h/\cos \gamma_F))=\arctan ((3.75-0.50)/(4/\cos 15))\approx \arctan 0.78\approx 38.13°$. The other twisting angles $\alpha$ to be set are calculated in analogy.

When approximating the measuring point 103 where the infrared temperature measuring head 20, in the direction of travel of the construction machine, is arranged essentially perpendicularly to the surface 110 of the road building material 50, the twisting angle is $\alpha=\arctan ((3.75-14d)/(h/\cos \gamma_F))=\arctan ((3.75-3.50)/(4/\cos 15))\approx \arctan 0.06\approx 3.45°$. When reaching the measuring point 103, the twisting angle $\alpha$ to be set consequently is 0°, since the infrared temperature measuring head 20 is again in the so-called zero position. The following twisting angles to be set are calculated in analogy to the calculations performed so far and use the angle $\beta$ for calculation. Consequently, the first twisting angle following after the measuring point 103 and directed in the direction of the right outer edge 112 is $\beta=\arctan ((3.75-14d)/(h/\cos \gamma_F))=\arctan ((3.75-3.50)/(4/\cos 15))\approx \arctan 0.06\approx 3.45°$. For the following measuring point 100 in a distance $d=0.25$ meters in the direction of the right outer edge 112, a twisting angle of $\beta=\arctan ((3.75-13d)/(h/\cos \gamma_F))=\arctan ((3.75-3.25)/(4/\cos 15))\approx \arctan 0.12\approx 6.88°$ is to be set. The subsequent twisting angle $\beta$ will then be $((3.75-12d)/(h/\cos \gamma_F))=\arctan ((3.75-3.00)/(4/\cos 15))\approx \arctan 0.18\approx 10.27°$. The further twisting angles $\beta$ to be set of the infrared temperature measuring head 20 are calculated in analogy.

In FIG. 4, due to the offset position 10 of the device, the angle $\alpha$ of about 60° is considerably larger than the angle $\beta$. The infrared temperature measuring head 20, however, may be twisted by a very large overall angle $(\alpha+\beta)$ of about 120° to 130°, for example. However, in order to ensure a measuring precision of $+/-3°$ C., it is advantageous for the infrared temperature measuring head 20 not to be twisted beyond a maximum value of the two angles $\alpha$ and $\beta$ of about 60° each relative to the, in the direction of movement of the construction machine, perpendicular distance line A. Nevertheless, with a positioning 10 of the device in accordance with FIG. 4, i.e., for example, with a fitting height h of the device in the region of about 4 meters above the surface 110 of the newly applied road building material 50 and a lateral distance $B_2$ to the outer edge 112 of about 1 meter, an overall mounting width $B=B_1+B_2=(\tan \alpha \times A)+1=(\tan \alpha \times (h/\cos 15))+1=(\tan 60 \times (4/\cos 15))+1\approx 7.1+1\approx 8.1$ meters can be detected. If the device is, relative to the direction of travel of the road finishing machine, arranged perpendicularly to the surface 110 at the road finishing machine, i.e. the fitting angle $\gamma_F=0°$ relative to the surface 110, the distance A of about 4 meters, in the present example, equals the fitting height h of the device above the surface 110.

With the example in accordance with FIG. 4, the first measuring point 100 to be recorded in the region of the outer edge 111 is in a distance of 7.00 meters starting from the measuring point 103 which represents the zero position mentioned already for the infrared temperature measuring head 20. Consequently, a first twisting angle $\alpha = \arctan (7.00/(h/\cos \gamma_F)) = \arctan (7.00/(4/\cos 15)) \approx \arctan 1.69 \approx 59.4°$ is set for the infrared temperature measuring head 20. For the following measuring point 100 in a distance d=0.25 meters in the direction of the right outer edge 112, a twisting angle of $\alpha = \arctan ((7.00-d)/(h/\cos \gamma_F)) = \arctan ((7.00-0.25)/(4/\cos 15)) \approx \arctan 1.63 \approx 58.47°$ is to be set. The subsequent twisting angle $\alpha$ will then be $\arctan ((7.00-2d)/(h/\cos \gamma_F)) = \arctan ((7.00-0.50)/(4/\cos 15)) \approx \arctan 1.57 \approx 57.5°$. The further twisting angles $\alpha$ to be set are calculated in analogy.

When approximating the measuring point 103 where the infrared temperature measuring head 20 is, in the direction of travel of the construction machine, arranged essentially perpendicularly to the surface 110 of the road building material 50, the twisting angle is $\alpha = \arctan ((7.00-27d)/(h/\cos \gamma_F)) = \arctan ((7.00-6.75)/(4/\cos 15)) \approx \arctan 0.06 \approx 3.45°$, in analogy to the example of the embodiment in accordance with FIG. 3. When reaching the measuring point 103, the twisting angle $\alpha$ to be set consequently is 0°, since the infrared temperature measuring head 20 will then again be in the zero position mentioned already. The subsequent twisting angles to be set are calculated in analogy to the example of the embodiment in accordance with FIG. 3. Consequently, the first twisting angle $\beta$ following after the measuring point 103 in the direction of the right outer edge 112 is $\beta \approx 3.45°$. For the following measuring point 100 in a distance d=0.25 meters in the direction of the right outer edge 112, a twisting angle of $\beta \approx 6.88°$ is to be set. The next twisting angle $\beta$ is $\approx 10.27°$. The further twisting angles $\beta$ to be set of the infrared temperature measuring head 20 are calculated in analogy.

In contrast to FIG. 4, in FIG. 5 the angle $\beta$ of about 60° is essentially larger than the angle $\alpha$. In addition, the fitting height h and, thus, the distance A of the device or the infrared temperature measuring head 20 to the surface 110 of the newly applied road surface 50 is smaller. Exemplarily, the fitting height h is about 3.5 meters. When assuming a lateral distance $B_1$ to the outer edge 111 of 2 meters, with this positioning 10 of the device, it is also possible to detect an overall mounting width $B = B_1 + B_2 = 2 + (\tan \beta \times A) = 2 + (\tan \beta \times (h/\cos 15)) = 2 + (\tan 60 \times (3.5/\cos 15)) \approx 8.2$ meters. With this example, too, the distance A of about 3.5 meters equals the fitting height h of the device above the surface 110, if the device is, relative to the direction of travel of the road finishing machine, arranged at the road finishing machine to be perpendicular to the surface 110, i.e. the fitting angle $\gamma_F = 0°$ relative to the surface 110.

With the example in accordance with FIG. 5, the first measuring point 100 to be recorded in the region of the outer edge 111 is in a distance $B_1$ of 2.00 meters starting from the measuring point 103 which represents the zero position mentioned already for the infrared temperature measuring head 20. Consequently, a first twisting angle $\alpha = \arctan (2.00/(h/\cos \gamma_F)) = \arctan (2.00/(3.5/\cos 15)) \approx \arctan 0.55 \approx 28.9°$ is set for the infrared temperature measuring head 20. For the following measuring point 100 in a distance d=0.25 meters in the direction of the right outer edge 112, a twisting angle of $\alpha = \arctan ((2.00-d)/(h/\cos \gamma_F)) = \arctan ((2.00-0.25)/(3.5/\cos 15)) \approx \arctan 0.48 \approx 25.78°$ is to be set. The next twisting angle $\alpha$ will then be $\arctan ((2.00-2d)/(h/\cos \gamma_F)) = \arctan ((2.00-0.50)/(3.5/\cos 15)) \approx \arctan 0.41 \approx 22.49°$. The further twisting angles $\alpha$ to be set are calculated in analogy.

When approximating the measuring point 103 where the infrared temperature measuring head 20 is, in the direction of travel of the construction machine, arranged to be essentially perpendicular to the surface 110 of the road finishing machine 50, the twisting angle $\alpha = \arctan ((2.00-7d)/(h/\cos \gamma_F)) = \arctan ((2.00-1.75)/(3.5/\cos 15)) \approx \arctan 0.07 \approx 3.95°$. When reaching the measuring point 103, the twisting angle $\alpha$ to be set consequently is 0° since the infrared temperature measuring head 20 will then again be in the zero position mentioned already. The following twisting angles to be set are calculated in analogy to the example of the embodiment in accordance with FIGS. 3 and 4, however, with a fitting height h=3.5 meters. Thus, the first twisting angle $\beta$ following after the measuring point 103 in the direction of the right outer edge 112 is $\beta \approx 3.95°$. For the following measuring point 100 in a distance d=0.25 meters in the direction of the right outer edge 112, a twisting angle of $\beta \approx 7.86°$ is to be set. The following twisting angle $\beta$ will then be $\approx 11.69°$. The further twisting angles $\beta$ to be set of the infrared temperature measuring head 20 are calculated in analogy.

FIG. 6 basically shows the device arranged at the road finishing machine in accordance with FIG. 5, wherein the device in FIG. 6 is arranged to be twisted by a fitting angle $\gamma_S$ in the range of about 15° in the scan direction of the infrared temperature measuring head 20. Such a twisting is usually caused by fitting which, however, is not necessarily required for detecting the overall mounting width B of the newly applied road surface 50 and has no influence on the operating behavior of the device itself, nor on the infrared temperature measuring head 20.

As far as the controller of the motor 30 which twists the infrared temperature measuring head 20 transverse to the direction of travel of the construction machine is concerned, the calculations are done in analogy to that of FIG. 5, wherein the fitting angle $\gamma_S$ is taken into consideration in the calculation. Thus, the first measuring point 100 to be recorded in the region of the outer edge 111 is also in a distance $B_1$ of 2.00 meters starting from the measuring point 103 which represents the zero position mentioned already for the infrared temperature measuring head 20. Consequently, a first twisting angle $\alpha + \gamma_S = \arctan (2.00/(h/\cos \gamma_F)) + \gamma_S = \arctan (2.00/(3.5/\cos 15)) + 15 \approx \arctan 0.55 + 15 \approx 43.9°$ is set for the infrared temperature measuring head 20. For the following measuring point 100 in a distance d=0.25 meters in the direction of the right outer edge 112, a twisting angle of $\alpha + \gamma_S = \arctan ((2.00-d)/(h/\cos \gamma_F)) + \gamma_S = \arctan ((2.00-0.25)/(3.5/\cos 15)) + 15 \approx \arctan 0.48 + 15 \approx 40.78°$ is to be set. The subsequent twisting angle $\alpha + \gamma_S$ will then be $\arctan ((2.00-2d)/(h/\cos \gamma_F)) + \gamma_S = \arctan ((2.00-0.50)/(3.5/\cos 15)) + 15 \approx \arctan 0.41 + 15 \approx 37.49°$. The further twisting angles $\alpha + \gamma_S$ to be set are calculated in analogy.

When approximating the measuring point 103 where the infrared temperature measuring head 20 is, in the direction of travel of the construction machine, arranged to be essentially perpendicular to the surface 110 of the road building material 50, the twisting angle is $\alpha + \gamma_S = \arctan ((2.00-7d)/(h/\cos \gamma_F)) + \gamma_S = \arctan ((2.00-1.75)/(3.5/\cos 15)) + 15 \approx \arctan 0.07 \approx 18.95°$. When reaching the measuring point 103, the twisting angle $\alpha + \gamma_S$ to be set will consequently be 15°, since the infrared temperature measuring head 20 will then again be in the zero position mentioned already. The following twisting angles to be set are calculated also in analogy to the embodiment in accordance with FIG. 5, however, taking into consideration the fitting angle $\gamma_S$ as well. Thus, the first twisting angle following after the measuring point 103 in the direction of the right outer edge 112 is $\beta-\gamma_S\approx-11.05°$. For the following measuring point 100 in a distance d=0.25 meters in the direction of the right outer edge 112, a twisting angle of $\beta-\gamma_S\approx-7.14°$ is to be set. The following twisting angle $\beta-\gamma_S$ will then be $\approx-3.31°$.

Figure 7:
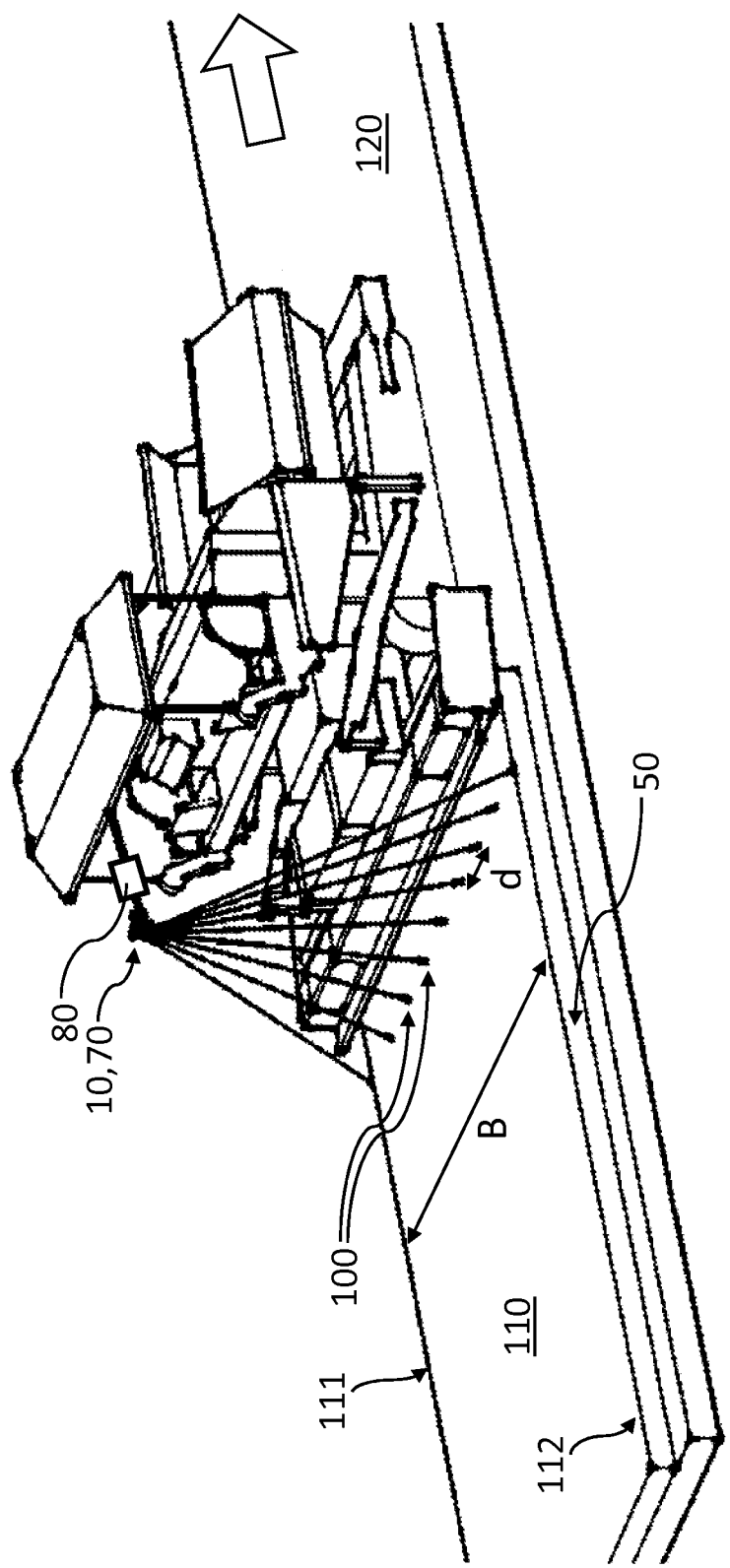
FIG. 7 shows a schematic illustration of a road finishing machine comprising an inventive device arranged at the back end thereof.

The road finishing machine schematically illustrated in FIG. 7 comprises the inventive device at its back end at the position 10. The direction of travel of the road finishing machine is illustrated by an arrow on the ground 120. A distance measurer 70, for example a laser distance measurer, and a weather station 80, which exemplarily determines the wind speed and the ambient temperature in the region of the road finishing machine, are also arranged in the region of the inventive device. The inventive device measures the temperature of the surface 110 of the newly applied road surface 50 over the mounting width B which is limited laterally, i.e. transverse to the direction of travel of the road finishing machine, by the outer edges 111 and 112. Thus, the measuring values are recorded at the measuring points 100 illustrated schematically and arranged in equal distances d transverse to the direction of travel of the road finishing machine. When the road finishing machine moves in the direction of travel, the scan movement of the infrared temperature measuring head 20 results in measuring points 100 on a line of a series of measurements which, when observed in reality, is diagonal. In this context, it is to be mentioned that the illustration of the points in FIGS. 7 and 8 is purely schematic and only serves to understand the mode of functioning of the device.

Figure 8:
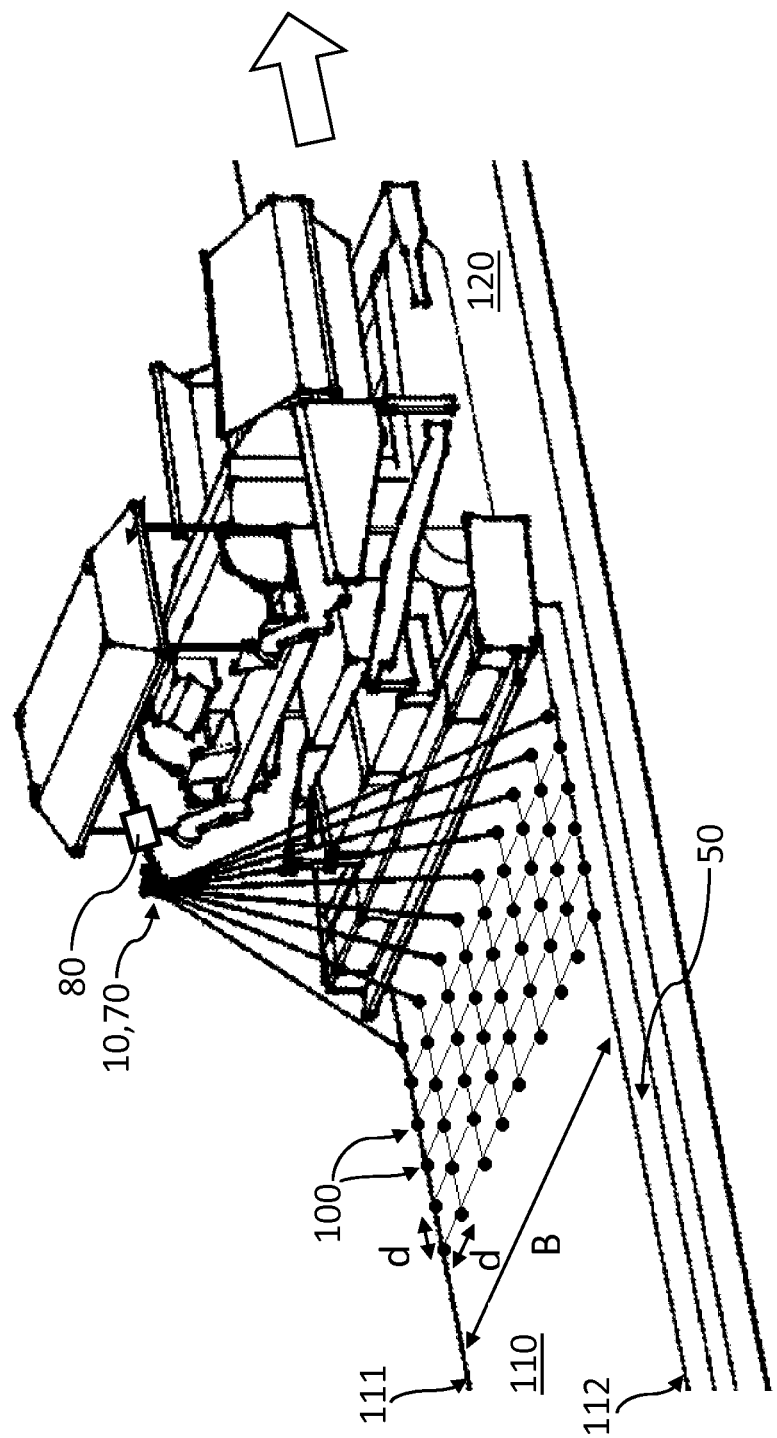
FIG. 8 shows a schematic illustration of the road finishing machine illustrated in FIG. 7 comprising a measuring point pattern illustrated schematically on the surface of the newly applied road building material.

FIG. 8 basically shows the road finishing machine of FIG. 7, however, with a measuring point pattern illustrated schematically on the surface 110 of the newly applied road building material 50 and directly behind the asphalt plank. The measuring points 100 thus exhibit equal distances d relative to one another both transverse to the direction of travel of the construction machine and in the direction of travel of the construction machine such that a steady measuring point pattern results behind the asphalt plank over the entire mounting width B of the newly applied road building material 50.

While this invention has been described in terms of several embodiments, there are alterations, permutations, and equivalents which will be apparent to others skilled in the art and which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

LIST OF REFERENCE NUMERALS

10 Fitting position of the device
15 Casing
16 Opening
20 Infrared temperature measuring head
25 Infrared radiation
30 Motor
40 Controller
50 Road building material
50a Ground
70 Distance measurer
80 Weather station
100 Measuring point
101, 102, 103 Measuring point
110 Surface
111, 112 Outer edges
120 Ground
d Distance between two measuring points
h Fitting height
A Distance
$\alpha, \beta$ Angles
$\gamma_S, \gamma_F$ Fitting angles of the device (S=scan direction; F=direction of travel)
B Mounting width
$B_1, B_2$ Width
b Direction of travel
$S_1, S_2$ Infrared radiation at the outer edges

The invention claimed is:

1. A device for determining the temperature of a road building material applied by a construction machine in a mounting width, comprising:
    an infrared temperature measuring head,
    a motor, and
    a controller, wherein
    the infrared temperature measuring head is arranged to be twistable by the motor transverse to the direction of travel of the construction machine and to record temperature measuring values of the surface of the road building material during a rotational movement at at least two measuring points spaced apart from one another,
    the device is freely mountable to the construction machine at different fitting positions,
    the controller controls, when fitting the device at the construction machine in a region within the mounting width, the motor based on a fitting position of the device at the construction machine such that a distance between measuring points on the surface to be measured remains equal irrespective of the fitting position of the device, and
    at least one of (i) the distance between the measuring points, and (ii) a duration of a temperature measurement of at least one of the measuring points, is adjustable.

2. The device in accordance with claim 1, wherein the controller controls the motor additionally based on fitting angles of the device at the construction machine.

3. The device in accordance with claim 1, wherein the controller changes a speed of movement of the infrared temperature measuring head in dependence on the speed of travel of the construction machine.

4. The device in accordance with claim 1, wherein the controller changes the direction of movement of the infrared temperature measuring head as soon as the measured temperature falls below a predetermined minimum value at at least one measuring point.

5. The device in accordance with claim 4, wherein the position where the infrared temperature measuring head changes its direction of movement is stored in the controller or in an evaluating unit arranged at the device or at the construction machine for calculating the mounting width of the newly applied road building material.

6. The device in accordance with claim 1, wherein the distance of the measuring points and/or the duration of the temperature measurement at a measuring point is/are settable.

7. The device in accordance with claim 1, wherein the device comprises a contactless distance measurer to measure the distance of the infrared temperature measuring head to the measuring point where the infrared temperature measuring head is directed to the surface of the road building material essentially perpendicularly.

8. The device in accordance with claim 7, wherein the contactless distance measurer is electrically connected to the controller.

9. The device in accordance with claim 1, wherein the controller is connectable electrically to a weather station arranged at the construction machine which determines a wind speed, ambient temperature, air humidity, rainfall and/or another ambient parameter in the region of the construction machine.

10. The device in accordance with claim 1, wherein the motor is a stepper motor, a servomotor, a direct-current motor or a direct-current motor comprising a gear unit.

11. A construction machine comprising at least one device in accordance with claim 1, wherein the device is arranged in the back region and/or in the front region of the construction machine.

* * * * *